(12) United States Patent
Galea et al.

(10) Patent No.: US 8,574,309 B2
(45) Date of Patent: Nov. 5, 2013

(54) TWO-STAGE SYSTEM AND METHOD FOR OXYGENATING AND REMOVING CARBON DIOXIDE FROM A PHYSIOLOGICAL FLUID

(75) Inventors: Anna Galea, Stow, MA (US); Gordon B. Hirschman, Cohoes, NY (US); Thieu Q Truong, North Easton, MA (US); Nicholas Vitale, Albany, NY (US)

(73) Assignee: Vivonics, Inc., Waltham, MA (US)

( * ) Notice: Subject to any disclaimer, the term of this patent is extended or adjusted under 35 U.S.C. 154(b) by 212 days.

(21) Appl. No.: 12/931,764

(22) Filed: Feb. 10, 2011

(65) Prior Publication Data

US 2012/0209399 A1    Aug. 16, 2012

(51) Int. Cl.
*A61F 2/04* (2013.01)
*A61M 37/00* (2006.01)

(52) U.S. Cl.
USPC ............................. 623/23.65; 604/6.14

(58) Field of Classification Search
USPC .................. 623/23.65; 604/264, 4.01–6.16
See application file for complete search history.

(56) References Cited

U.S. PATENT DOCUMENTS

| | | | |
|---|---|---|---|
| 5,492,109 A | 2/1996 | Hirschl et al. | |
| 7,498,275 B2* | 3/2009 | Monzyk et al. | 442/45 |
| 2002/0143397 A1 | 10/2002 | Von Segesser | |
| 2004/0009096 A1* | 1/2004 | Wellman | 422/44 |
| 2007/0276508 A1* | 11/2007 | Fischer et al. | 623/23.65 |
| 2009/0018484 A1* | 1/2009 | Levitov | 604/6.14 |
| 2010/0145471 A1* | 6/2010 | Johns | 623/23.65 |
| 2011/0038760 A1* | 2/2011 | Monzyk et al. | 422/119 |
| 2011/0129389 A1* | 6/2011 | Brady et al. | 422/48 |
| 2011/0158847 A1* | 6/2011 | Charest et al. | 422/45 |
| 2011/0160517 A1* | 6/2011 | Smith et al. | 600/16 |
| 2011/0190679 A1* | 8/2011 | Humes et al. | 604/4.01 |
| 2012/0330438 A1* | 12/2012 | Keshavjee et al. | 623/23.65 |

OTHER PUBLICATIONS

Written Opinion of International Application No. PCT/US2011/000236, from the International Searching Authority, dated Apr. 8, 2011, 6 pgs. (unnumbered).

* cited by examiner

*Primary Examiner* — Suzette J Gherbi
(74) *Attorney, Agent, or Firm* — Iandiorio Teska & Coleman, LLP

(57) ABSTRACT

A two-stage system for oxygenating and removing carbon dioxide from a physiological fluid, including: a primary exchange module configured to receive a gas having oxygen therein and a carrier fluid having carbon dioxide therein. The primary exchange module is configured to transfer oxygen from the gas to the carrier fluid and transfer carbon dioxide from the carrier fluid to the gas to create an oxygen loaded carrier fluid and a carbon dioxide load gas. A secondary exchange module is configured to receive the oxygen loaded carrier fluid and a physiological fluid having the carbon dioxide therein. The secondary exchange module is configured to transfer the oxygen from the oxygen loaded carrier fluid to the physiological fluid and transfer carbon dioxide from the physiological fluid to the carrier fluid to create an oxygen loaded physiological fluid.

29 Claims, 15 Drawing Sheets

TWO-STAGE SYSTEM AND METHOD FOR OXYGENATING AND REMOVING CARBON DIOXIDE FROM A PHYSIOLOGICAL FLUID

GOVERNMENT RIGHTS

This invention was made with U.S. Government support under Grant Nos. 6R43HL074456-02 and 1R43HL091593-01, both awarded by the National Institutes of Health. The United States Government may have certain rights in certain aspects of the invention.

FIELD OF THE INVENTION

This invention relates to a two-stage system and method for oxygenating and removing carbon dioxide from a physiological fluid.

BACKGROUND OF THE INVENTION

The main function of lungs is to transfer oxygen from the atmosphere into the blood and expel carbon dioxide therefrom to the atmosphere. For patients with diseased or damaged lungs, there are few options. Some of the most common diseases leading to end-stage lung failure include, inter alia, chronic obstructive pulmonary disease (COPD), cystic fibrosis (CF), idiopathic pulmonary fibrosis (IPF), and pulmonary hypertension (PH). There are also many people suffering from lung cancer and poor lung function due to years of smoking who are not eligible for a lung resection or lung transplantation.

Lung transplantation remains the main therapy for chronic irreversible respiratory failure. However, only about 1,000 procedures are performed each year due to the severe shortage of suitable donor organs. See, e.g., Franco et al.: "Heart-Lung Transplantation for Cystic Fibrosis," Journal of Applied Cardiology 4:571 (1989). The most common indications for lung transplantation include COPD, CF, IPF, and PH. Patients with lung cancer are not candidates for transplantation because the use of immunosuppression could potentially cause the cancer to spread. Lung transplant candidates can die waiting for an organ donor since the average waiting time period may exceed two years. The overall results are not ideal due to the extensive surgery required, deterioration of the patient's condition during the waiting period, the complications of chronic immunosuppression, infection, and the development of chronic rejection. Also, many patients with chronic lung disease tend to be older individuals who are poor candidates for transplantation because they do not tolerate immunosuppression.

Xenotransplantation has been explored as an option to solve the donor shortage, but success remains years away until the cross-species immunologic barriers can be completely overcome, see et al., Higgins et al.: "Improved Ultrastructural Lung Preservation with Prostaglandin El as Donor Pre-treatment in a Primate Heart-Lung Transplant Model", JTHCVS 105:965 (1993). Advances in xenotransplantation are occurring but clinical trials are still in the future, and the first use of such organs would probably be closely related to the current human lung transplantation surgery. Although xenotransplantation would help with the donor shortage, it would not solve many of the other issues involved with human lung transplantation, such as immunosuppression.

Another option for patients suffering from diseased or damaged lungs may be to utilize an enriched oxygen supply, frequently in conjunction with a ventilator. However, this has been shown to create dependency and a host of other ventilator-related disorders. See e.g., Candadai et al., "Weaning success among ventilator-dependent patients in a rehabilitation facility", Arch Phys Med Rehabil 2002; 83:154-7; Slutsky, A. S., "Lung Injury Caused by Mechanical Ventilation." CHEST, vol. 116 no. suppl. 19S-15S, July 1999).

The concept of using an artificial lung in clinical medicine to take over the gas exchange function of diseased or damaged lung(s) dates back to the development of the heart-lung machine in 1954. Cardiopulmonary bypass (CPB) is a technique used to take over the function of the heart and lungs during surgery by regulating the circulation of blood and oxygen within a person's body. The artificial lung may provide short-term pulmonary support during extensive operations on the heart.

Over the last 20 years, several conventional mechanical-assisting devices have been developed to treat diseased or damaged lung(s) acute reversible respiratory failure due to acute respiratory distress syndrome (ARDS). Conventional systems have also been developed for short-term pulmonary support (e.g., days to a few weeks). These systems include extracorporeal membrane oxygenation (ECMO) devices, extracorporeal carbon dioxide removal ($ECCO_2R$) devices, and intravascular oxygenators (IVOX) devices.

Although conventional ECMO and IVOX systems have been used for aiding patients with diseased or damaged lung(s), they are both one-stage systems with distinct drawbacks. ECMO devices produce significant complication rates and typically do not provide a significant improvement. IVOX devices may alleviate some of the problems associated with ECMO devices. However, the gas exchange area of IVOX devices may be too small and the device may not provide the needed total support for gas exchange. Also, IVOX devices may not take away excess carbon dioxide leftover within the system. $ECCO_2R$ and ECMO are also one-stage systems and may be limited by the inclusion of fibers that come in contact with blood thereby causing blood activation and thrombogenesis.

In the past decade, IVOX systems have been the primary focus for treating diseased or damaged lung(s). Conventional one-stage IVOX systems typically include membranous or fibrous components used for oxygenation. Typically, a bundle of hollow fibers may be used as the oxygenating element. Exposing blood to the large artificial surface area needed for gas exchange often causes blood activation and thrombogenesis.

There has also been some research in utilizing an oxygen-carrying liquid to bring oxygen directly to the blood, however this research has focused on using small bubbles of liquid that are injected into the blood and then removed using a selective filter. When bubbles of fluid are injected into the blood, the system typically requires a means for pulling the bubbles out of the blood before it flows back into a user, which may also cause blood activation. These systems typically do not appreciably decrease the amount of carbon dioxide in the blood.

BRIEF SUMMARY OF THE INVENTION

This invention features a two-stage system for oxygenating and removing carbon dioxide from a physiological fluid, the system including a primary exchange module configured to receive a gas having oxygen therein and an carrier fluid having carbon dioxide therein. The primary exchange module is configured to transfer oxygen from the gas to the carrier fluid and transfer carbon dioxide from the carrier fluid to the gas to create an oxygen loaded carrier fluid and a carbon dioxide load gas, and a secondary exchange module is configured to receive the oxygen loaded carrier fluid and a physiological fluid having the carbon dioxide therein. The secondary exchange module configured to transfer the oxygen from the oxygen loaded carrier fluid to the physiological fluid and transfer carbon dioxide from the physiological fluid to the carrier fluid to create an oxygen loaded physiological fluid.

In one embodiment, the primary exchange module may include a gas and fluidic distribution subsystem including one or more of: a gas inlet configured to receive the gas having the oxygen therein, a fluidic inlet in fluidic communication with the secondary exchange module configured to receive the carrier fluid having carbon dioxide therein, a fluidic outlet in fluidic communication with the secondary exchange module configured to transfer the oxygen loaded carrier fluid to the secondary exchange module, and a gas outlet configured to expel the carbon dioxide loaded gas from the primary exchange module. The gas having the oxygen therein gas may include one or more of: ambient air, oxygen gas, and a gas containing oxygen. The secondary exchange module may include a fluidic distribution subsystem including one or more of: a first fluidic inlet in fluidic communication with the primary exchange module configured to receive the oxygen loaded carrier fluid, a second fluidic inlet in fluidic communication with the physiological fluid having the carbon dioxide therein, a first fluidic outlet in fluidic communication with the primary exchange module configured to transfer the carrier fluid having carbon dioxide therein to the primary exchange module, and a second fluidic outlet configured to transfer the oxygen loaded physiological fluid to the vascular system of the patient. The second fluidic inlet and/or the second fluidic outlet may be coupled to the vascular systems of a patient. The primary exchange module may include at least one array having plurality of hollow fibers configured to receive the gas having the oxygen therein and in fluidic communication with the carrier fluid having carbon dioxide therein. The at least one array configured to provide the transfer of the oxygen from the gas to the carrier fluid and the transfer of the carbon dioxide from the carrier fluid to the gas. The distance between one or more and/or each of the plurality of hollow fibers may be configured to provide the transfer of oxygen and said transfer of carbon dioxide. The plurality of fibers may be configured such that the distance between one or more and/or each of the plurality of fibers is smaller than or equal to the outer diameter of one or more and/or each of the plurality of fibers. The at least one array may include a plurality of headers configured to align the plurality of hollow fibers in a predetermined orientation. The secondary exchange module may include at least one microfluidic channel in fluidic communication with the oxygen loaded carrier fluid and the physiological fluid having carbon dioxide therein configured to create a parallel flow of the oxygen loaded carrier fluid and the physiological fluid having carbon dioxide therein to provide said transfer of oxygen and said transfer of carbon dioxide. The at least one microfluidic channel may be configured with a predetermined height to create the parallel flow. The at least one microfluidic channel may be configured with a predetermined height to reduce the Reynolds number such that the effective viscosity of the oxygen loaded carrier fluid and the physiological fluid is increased to maintain said parallel flow. The predetermined height may be less than or equal to about 1 mm. The at least one microfluidic channel may include at least two opposing surfaces. The opposing surfaces may be coated with and/or made of a material configured to stabilize and further separate said parallel flow. One of the opposing surfaces may be coated with and/or made of a material having hydrophilic properties configured to attract the physiological fluid and repel the oxygen loaded carrier fluid to stabilize and further separate said parallel flow. One of the opposing surfaces may be coated with and/or made of a material having hydrophobic properties configured to attract the oxygen loaded carrier fluid and repel the physiological fluid to stabilize and further separate said parallel flow. The carrier fluid and the physiological fluid may be configured to be immiscible with each other to stabilize and further separate said parallel flow. The at least one microfluidic channel may include a predetermined shape configured to increase the surface area of the microfluidic channel in relation to the cross-sectional area of the microfluidic channel to stabilize and separate said parallel flow. The predetermined shape may include one or more of: a rectangular shape, a circular shape, an offset circular shape, and a scallop shape. The at least one microfluidic channel may be made of bio-compatible material. The at least one microfluidic channel may be housed in a chamber. The at least one microfluidic channel may include a plurality of microfluidic channels. The carrier fluid may include perfluorocarbon. The primary exchange module may include a blower and/or plurality of bellows configured to deliver the gas having oxygen therein thereto. The primary exchange module and the secondary exchange module may be located external from the patient. The primary exchange module and the secondary exchange module may be implanted within a patient. The primary exchange module and the secondary exchange module may be configured in the shape of a lung. The lung may be implanted within a patient.

This invention also features a two-stage method for oxygenating and removing carbon dioxide from a physiological fluid, the method including providing a first stage configured to receive a gas having oxygen therein, receive an carrier fluid having carbon dioxide, and transfer oxygen from the gas to the carrier fluid and transfer carbon dioxide from the carrier fluid to the gas to create an oxygen loaded carrier fluid and a carbon dioxide loaded gas. A second stage is configured to receive the oxygen loaded carrier fluid, receive a physiological fluid having the carbon dioxide therein, and transfer the oxygen from the oxygen loaded carrier fluid to the physiological fluid and transfer carbon dioxide from the physiological fluid to the carrier fluid to create an oxygen loaded physiological fluid.

In one embodiment, receiving the physiological fluid may include receiving a physiological fluid from the vascular system of a patient. The method may include the step of transferring the oxygen loaded physiological fluid to the vascular system of a patient. The method may include the step of creating a parallel flow of the oxygen loaded carrier fluid and the physiological fluid having carbon dioxide therein to provide the transfer of the oxygen from the oxygen loaded carrier fluid to the physiological fluid and the transfer of the carbon dioxide from the physiological fluid to the carrier fluid. The method may include the step of stabilizing and further separating said parallel flow. The method may include the step of increasing the effective viscosity of the oxygen loaded carrier fluid and the physiological fluid to maintain said parallel flow.

BRIEF DESCRIPTION OF THE SEVERAL VIEWS OF THE DRAWINGS

Other objects, features and advantages will occur to those skilled in the art from the following description of the embodiments and the accompanying drawings, in which.

DETAILED DESCRIPTION OF THE INVENTION

Figure 1:
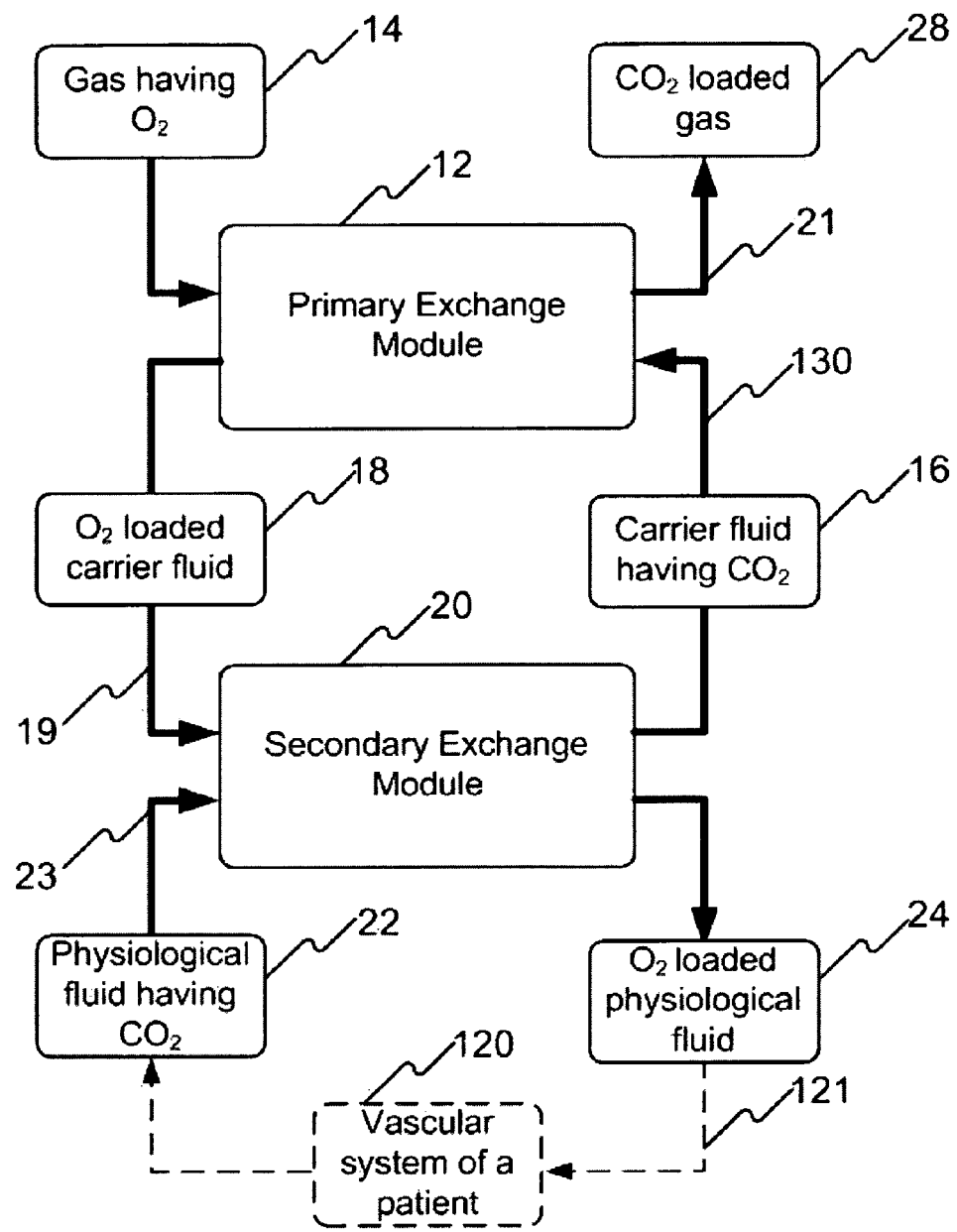
FIG. 1 is a block diagram showing the primary components of one embodiment of the two-stage system for oxygenating and removing carbon dioxide from a physiological fluid of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one embodiment of two-stage system 10 for oxygenating and removing carbon dioxide from a physiological fluid. System 10 includes primary exchange module 12 configured to receive gas 14 having oxygen therein and carrier fluid 16 having carbon dioxide therein. In one example the gas having oxygen therein may include ambient air, an oxygen gas, or any gas having oxygen therein. Carrier fluid 16 is preferably immiscible with respect to physiological fluid 22 and may be made of a perfluorocarbon, such as a perfluorodecalin ($C_{10}F_{18}$), or similar type compound known to those skilled in the art, that prevents carrier fluid 16 from mixing with physiological fluid 22 having carbon dioxide therein (discussed below). Primary exchange module 12 transfers oxygen from gas 14 having oxygen therein to carrier fluid 16 and transfers the carbon dioxide in carrier fluid 16 to gas 14 to create oxygen loaded carrier fluid 18 and carbon dioxide loaded gas 20. Carbon dioxide loaded gas is preferably expelled from primary exchange module 12, as shown at 21.

System 10 also includes secondary exchange module 20 which receives oxygen loaded carrier fluid 18 from primary exchange module 12, indicated at 19, and physiological fluid 22 having carbon dioxide therein indicated at 23. Physiological fluid 22 may include blood, serum, or any similar type physiological fluid having carbon dioxide therein. In one example, physiological fluid 22 having carbon dioxide therein may be received from vascular system of a patient 120. Secondary exchange module transfers the oxygen from oxygen loaded carrier fluid 18 to physiological fluid 22 and transfers carbon dioxide from physiological fluid 22 to produce oxygen loaded physiological fluid 24 and carrier fluid 16 having carbon dioxide therein. Oxygen loaded physiological fluid 24, which now has carbon dioxide removed, may then be transferred to vascular system of a patient 120, as shown at 121. Carrier fluid 16, having carbon dioxide therein, is transferred to primary exchange module 12, as shown at 130.

The result is system 10 receives physiological fluid 22 having carbon dioxide therein, effectively removes carbon dioxide therefrom and loads physiological fluid 22 with oxygen. Oxygen loaded physiological fluid 24 may be then transferred to vascular system of patient 120. Thus, system 10 can be used to effectively assist or replace the function of diseased or damaged lung(s) discussed in the Background section above. In one embodiment, system 10 may be used as an artificial lung. Because system 10 is a two-stage system, the problems discussed above with conventional systems, such as ECMO and IVOX, and the like, may be significantly reduced or eliminated.

Figure 2:
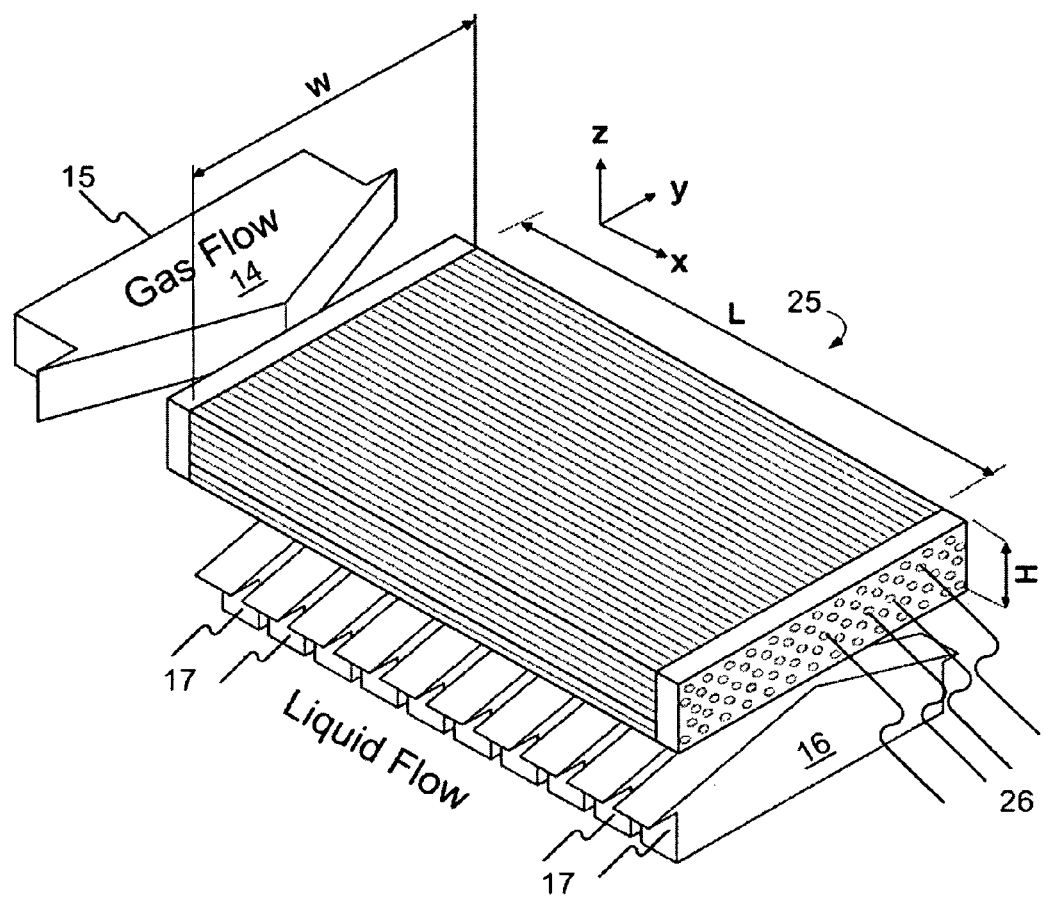
FIG. 2 is a three-dimensional view showing in further detail the primary exchange module shown in FIG. 1.

Primary exchange module 12 preferably includes at least one array, e.g., array 25, FIG. 2, which includes a plurality of hollow fibers 26 which receives gas 14 having oxygen therein. In one example, gas 14 enters hollow fibers 26 in the direction indicated by arrow 15 and flows through hollow fibers 26. Array 25 is preferably in fluidic communication with carrier fluid 16 having carbon dioxide therein. In one design, carrier fluid 16 having carbon dioxide flows into array 25, in the direction indicated by arrows 17 and travels about and in close proximity to each of the hollow fibers 26, e.g., as indicated by arrows 38, 40, 42, 44, 46, and 48, FIGS. 3A 48 (discussed below). Hollow fibers 26 efficiently transfer the oxygen in gas 14 to the carrier fluid 16 and efficiently transfer the carbon dioxide in carrier fluid 16 to the gas inside hollow fibers 26.

Figure 3A:
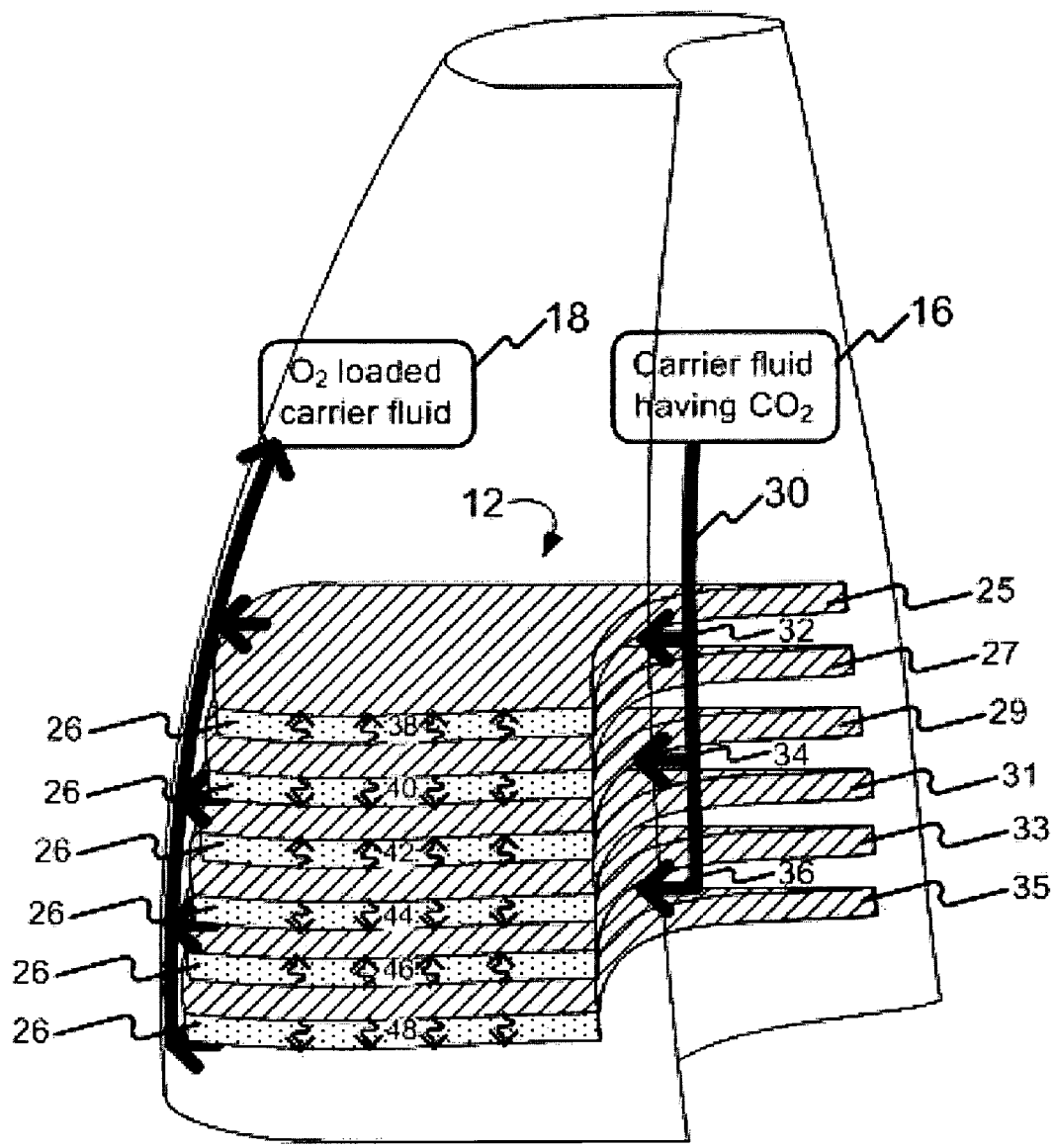
FIG. 3A is a three-dimensional view showing in further detail one example of the flow of the carrier fluid having carbon dioxide between hollow fibers shown in FIG. 2.
Figure 3B:
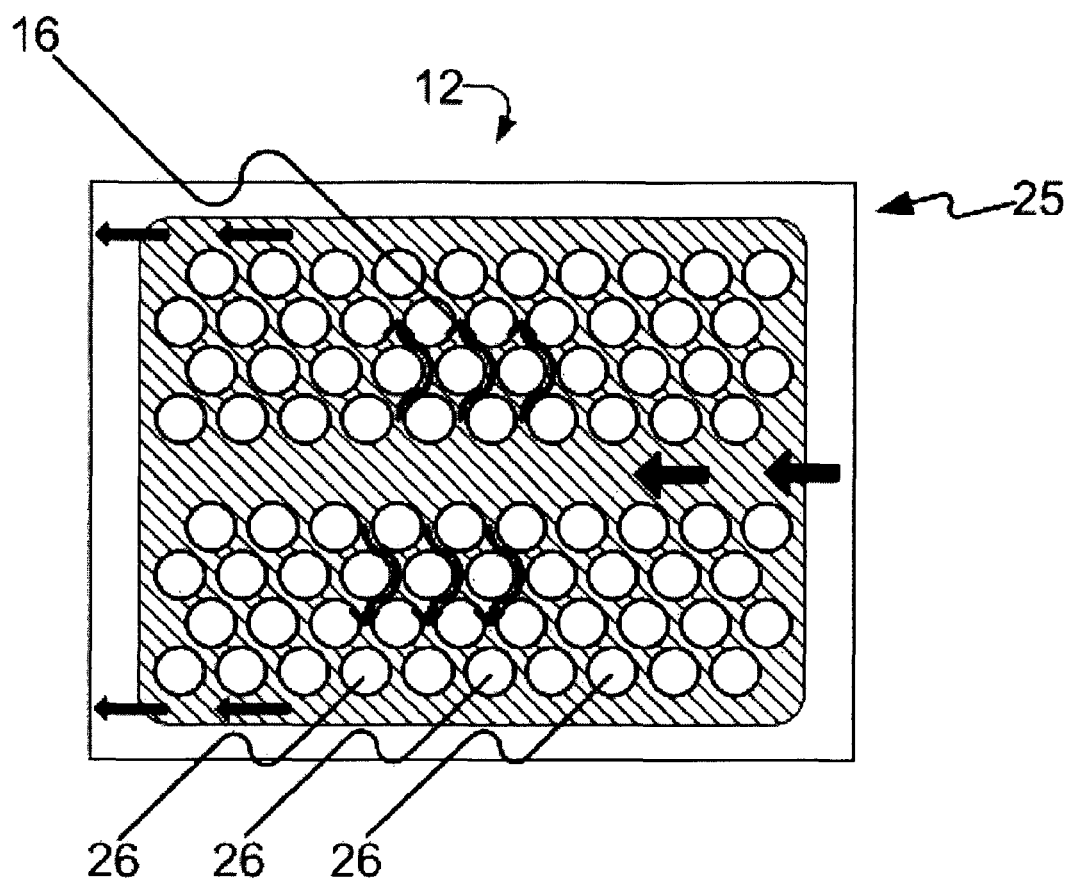
FIG. 3B is a schematic end-view showing the flow of the carrier fluid having carbon dioxide between hollow fibers shown in FIG. 2.

FIG. 3A shows one embodiment of primary exchange module 12 including a plurality of arrays, e.g., arrays 25, 27, 29, 31, 35. Each of arrays 25-35 similarly includes hollow fibers 26 as discussed above. In this example, carrier fluid 16 having carbon dioxide therein enters primary exchange module 12 by line 30 and then flows in between and the arrays as shown by arrows 32, 34, and 34. Carrier fluid 16 then travels in an upward and downward direction and flows in between and about hollow fibers 26 of arrays 25-35, indicated by arrows 38, 40, 42, 44, 46, and 48. When carrier fluid 16 travels in between, about, and in close proximity to, hollow fibers 26, hollow fibers 26 efficiently transfer the oxygen in gas 14, FIGS. 1-2, to carrier fluid 16 and transfer the carbon dioxide in carrier fluid 16 to the gas inside hollow fibers 26 to create oxygen loaded carrier fluid 18, FIG. 1 and carbon dioxide loaded gas 20. FIG. 3B is an end view array 25 of primary exchange module 12 and shows another example of the flow of carrier fluid 16 around, about, and in close proximity to hollow fibers 26 of array 25.

Figure 4:
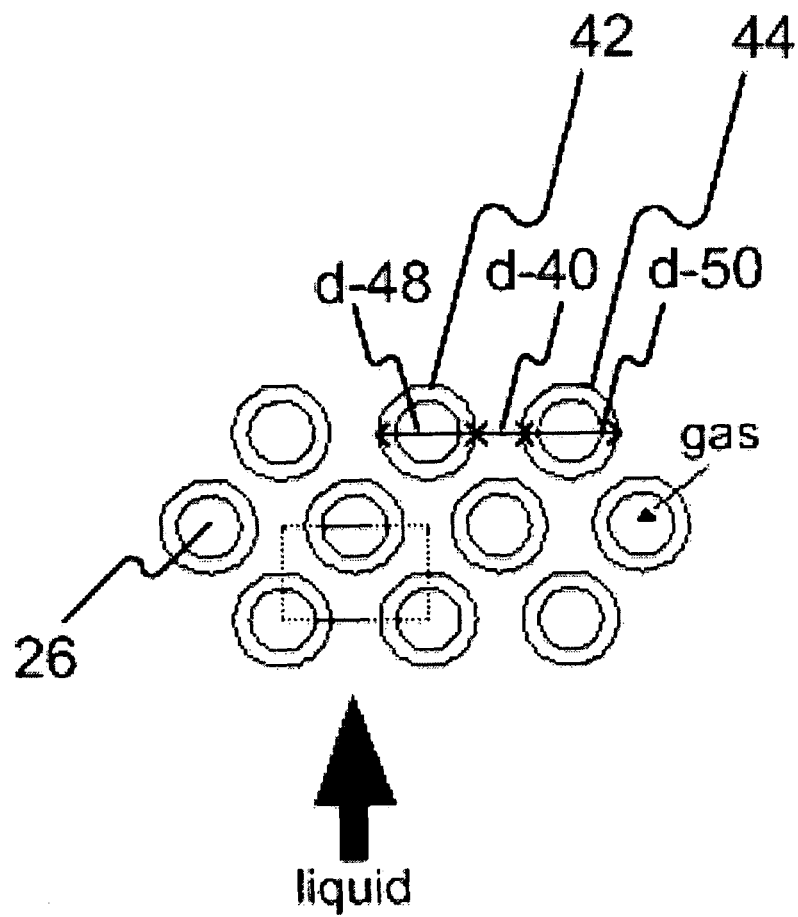
FIG. 4 is a schematic end-view showing in further detail one embodiment of the structure of the plurality of hollow fibers shown in FIGS. 2-3B.

In one embodiment, the distance between one or more, or each of, hollow fibers 26, FIGS. 2-3B, is preferably configured to provide the efficient transfer of the oxygen from the gas having oxygen therein to the carrier fluid and the transfer of the carbon dioxide from the carrier fluid to the gas as discussed above. In one example, the distance between one or more, or of each hollow fiber 26 is preferably smaller than or equal to the outer diameter hollow fibers 26. For example, distance d-40, FIG. 4, between hollow fiber 42 and hollow fiber 44 of the plurality of hollow fibers 26 is preferably smaller than or equal the outer diameter d-48 of fiber 42 and outer diameter d-50 of fiber 44. In one example, the distance d-40 is about 100 microns and outer diameter distances d-48 and d-50 are about 125 microns.

Figure 5:
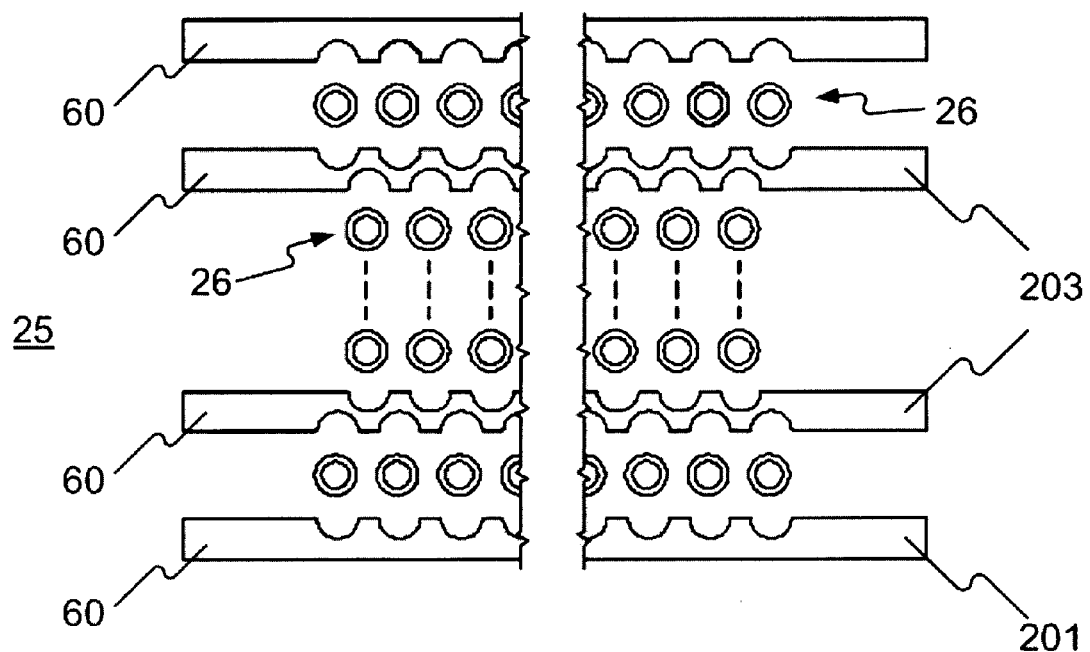
FIG. 5 is a schematic end-view showing one example of headers used to align the hollow fibers shown in FIGS. 2-3B in a predetermined orientation.

In one example, array 25, FIG. 2 preferably includes headers 60, FIG. 5, which align hollow fibers 26 in a closely packed configuration as shown in FIGS. 2-3B. Header 60 also preferably align hollow fibers 26 of the array(s) such that the distance between one or more of each of the hollow fibers 26 is smaller than or equal to the outer diameter of each of the plurality of fibers, as discussed above with reference to FIG. 4.

Figure 6A:
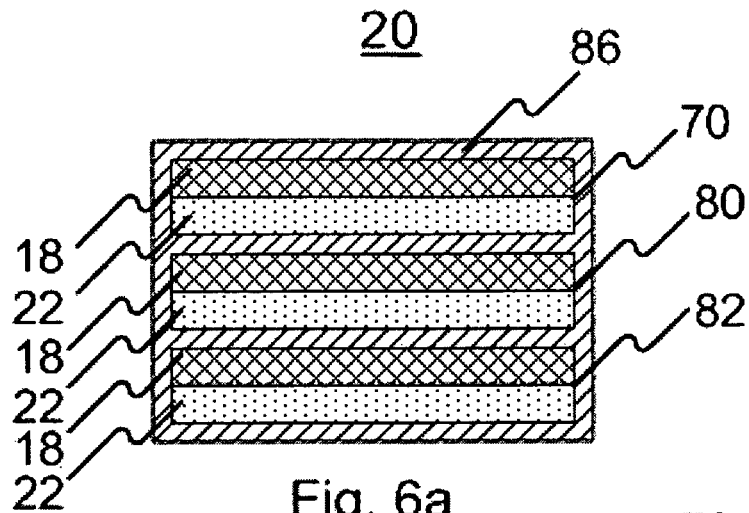
FIG. 6A is a schematic end-view showing one example of the structure of the microfluidic channel of the secondary exchange module shown in FIG. 1.

Secondary exchange module 20, FIG. 1, preferably includes at least one microfluidic channel 70, FIG. 6A, which is designed to create a parallel flow of oxygen loaded carrier fluid 18 and physiological fluid 22 having carbon dioxide therein. The parallel flow of oxygen loaded carrier fluid 18 and physiological fluid 22 having carbon dioxide therein provides the efficient transfer of oxygen and carbon dioxide between carrier fluid 18 and physiological fluid 22 to create oxygen loaded physiological fluid 22, and carrier fluid 16 having carbon dioxide therein, FIG. 1, as discussed above.

In one example, channel 70, FIG. 6A is preferably designed with a predetermined height to create the parallel flow of oxygen loaded carrier fluid 18 and physiological fluid 22 having carbon dioxide therein. Preferably, the predetermined height is less than or equal to about 1 mm. The height of channel 70 may also be designed to reduce the Reynolds number such that the effective viscosity of oxygen loaded carrier fluid 18 and physiological fluid 22 is increased to maintain the parallel flow. The length of channel 70 is preferably long enough such that the parallel flow of oxygen loaded carrier fluid 18 and physiological fluid 22 having carbon dioxide provides for efficiently transferring the oxygen and carbon dioxide as discussed above. In one example, length of channel 70 is about 0.5 mm to about 2.5 cm, although channel 70 may be any length as known by those skilled in the art.

Figure 6B:
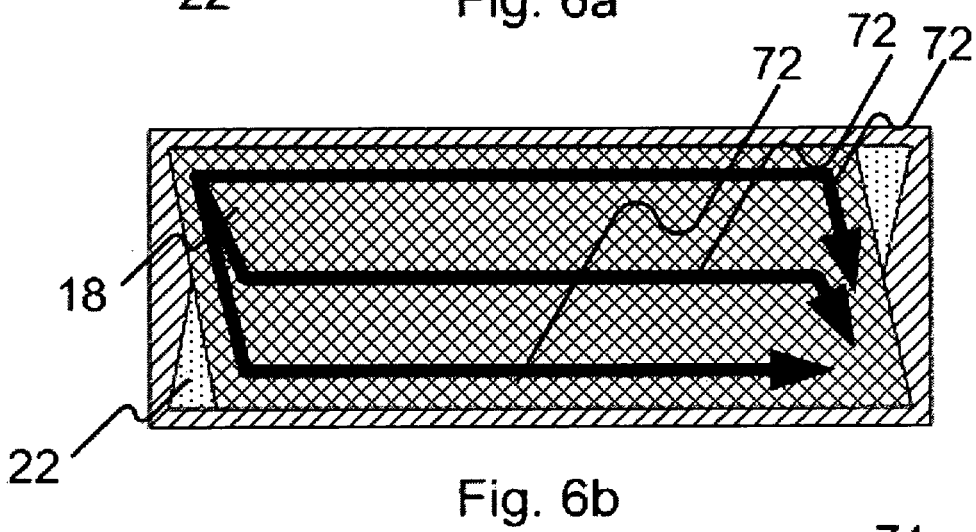
FIG. 6B is a schematic top-view of the microfluidic channel shown in FIG. 6A showing one example of oxygen loaded carrier fluid traveling over physiological fluid having carbon dioxide therein.
Figure 6C:
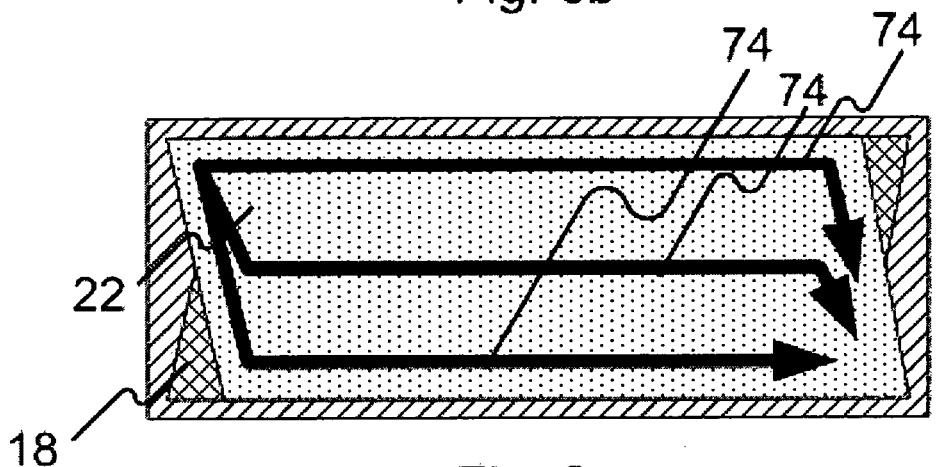
FIG. 6C is a schematic bottom-view of the microfluidic channel shown in FIG. 6 showing one example of the physiological fluid having carbon dioxide therein traveling under the oxygen loaded carrier fluid.

FIG. 6B shows a top view of one example of flow 72 of oxygen loaded carrier fluid 18 in parallel and flowing over physiological fluid 22 having carbon dioxide therein. FIG. 6C shows an example of a bottom view of channel 70 depicting flow 74 of physiological fluid 22 flowing parallel to and, in this example, under oxygen loaded carrier fluid 18. In other examples physiological fluid 22 may flow in parallel and over oxygen loaded carrier fluid 18.

In one design, secondary gas exchange module 20, FIG. 1, includes a plurality of channels, e.g., channels 70, 80, and 82, FIG. 6A. In this example, channel 70 creates a parallel flow of oxygen loaded carrier fluid 18 and physiological fluid 22 having carbon dioxide therein, as discussed above. Similarly, channel 80 creates a parallel flow of oxygen loaded carrier fluid 18 and physiological fluid 22 having carbon dioxide therein, and channel 82 creates a parallel flow of oxygen loaded carrier fluid 18 and physiological fluid 22 having carbon dioxide therein. In one example, the plurality of channel 70, 80, and 82 are housed in chamber 86.

Figure 7:
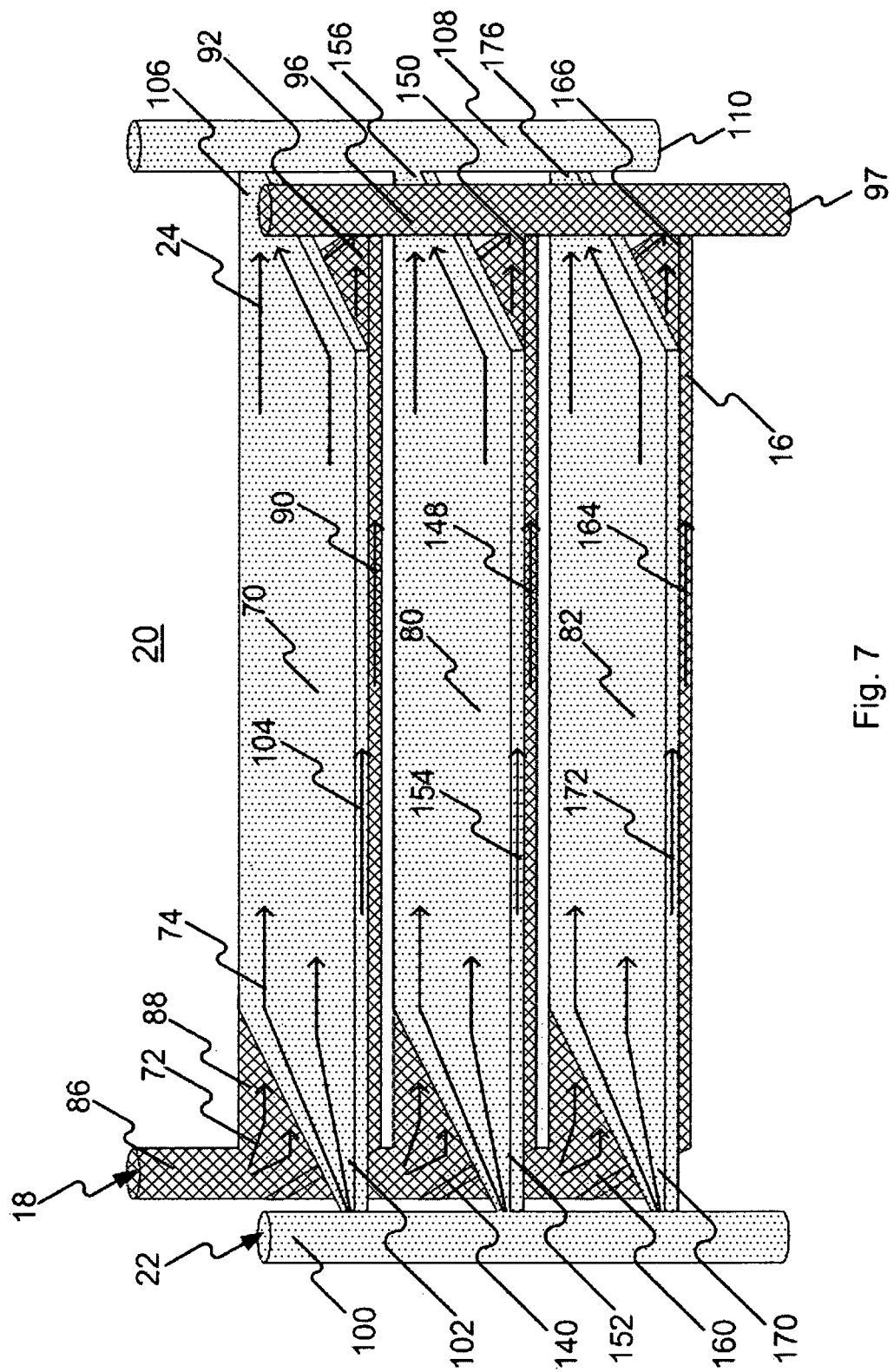
FIG. 7 is a three-dimensional front-view showing in further detail one embodiment of the microfluidic channels shown in FIG. 6A-C.

FIG. 7, where like parts have been given like numbers, shows in further detail one example of the structure of secondary exchange module 20 with channels 70, 80, and 82. In this example, oxygen loaded carrier fluid 18 flows into microtubule 86, enters channel 70 at inlet plenum 88, and then flows in the direction shown by arrows 90 to the far end of channel 70 where it exits channel 70 as carrier fluid 16 having carbon dioxide therein via outlet plenum 92. Carrier fluid 16 having carbon dioxide therein then flows into microtubule 96, travels down microtubule 96, and then exits secondary exchange module 20 via outlet 97. Carrier 16 having carbon dioxide therein is then transferred to primary exchange module 12, FIG. 1 and processed as discussed above. Physiological fluid 22 having carbon dioxide therein, FIGS. 1 and 7, e.g., from vascular system of a patient 120, FIG. 1, flows into microtubule 100, FIG. 7, enters channel 70 via inlet plenum 102, travels in the direction indicated by arrows 104 to the far end of channel 70 where it exits channel 70 as oxygen loaded physiological fluid 22 via a outlet plenum 106. Oxygen loaded physiological fluid 24 then flows into microtubule 108, travels down microtubule 108, and then exits secondary exchange module 20 via outlet 110. Oxygen loaded physiological fluid 22 may then be transferred back to vascular system of a patient 120, FIG. 1.

Similarly, oxygen loaded carrier fluid 18, FIG. 7, may flow into microtubule 86, enter channels 80, 82 at inlet plenums 140, 160, respectively, and then flows in the direction shown by arrows 148, 164 to the far end of channels 80, 82 where it exits channels 80, 82 as carrier fluid 16 having carbon dioxide therein via outlet plenums 150, 166, respectively. Carrier fluid 16 having carbon dioxide therein then flows into microtubule 96, travels down microtubule 96, and exits secondary exchange module 20 via outlet 97. Carrier 16 having carbon dioxide therein may be then transferred to primary exchange module 12, FIG. 1 where it is processed as discussed above. Physiological fluid 22 having carbon dioxide therein, FIGS. 1 and 7, e.g., from vascular system of a patient 120, flows into microtubule 100, FIG. 7, enters channels 80, 82 via inlet plenums 152, 170, respectively, travels in the direction indicated by arrows 154, 172 to the far end of channels 80, 82 where it exits channels 80, 82 as oxygen loaded physiological fluid 22 via a outlet plenums 156, 176, respectively. Oxygen loaded physiological fluid 24 then flows into microtubule 108, travels down microtubule 108, and then exits secondary exchange module 20 via outlet 110. Oxygen loaded physiological fluid 22 may then be transferred back to vascular system of a patient 20, FIG. 1.

As shown in FIG. 7, microfluidic channels 70, 80, and/or 82 create a parallel flow of oxygen loaded carrier fluid 18 and physiological fluid 22 having carbon dioxide therein. The parallel flow provides an efficient transfer of oxygen from oxygen loaded carrier fluid 18 to physiological fluid 22 having carbon dioxide therein and an efficient transfer of the carbon dioxide from physiological fluid 22 to the carrier fluid 16 to create oxygen loaded physiological fluid 22 and carrier fluid 16 having carbon dioxide therein. As discussed above, oxygen-loaded physiological fluid 22 has the carbon dioxide removed therefrom. Oxygen loaded physiological fluid 22 may then be transferred to vascular system of a patient 120, FIG. 1, and carrier fluid 16 having carbon dioxide therein is transferred to primary exchange module 12, as discussed above.

In one embodiment, microfluidic channel 70, FIGS. 6A, and 7, and/or microfluidic channels 80 and 82 may include opposing surfaces which may be coated with, or made of, a material configured to stabilize and further separate the parallel flow of oxygen loaded carrier fluid 18 and physiological fluid 22 having carbon dioxide therein. For example, one of opposing surfaces 180, 182, e.g. surface 180, FIG. 6A, may be coated, or made of, a material having hydrophobic properties which attract oxygen loaded carrier fluid 18 and repel physiological fluid 22. The other of surfaces 180, 182, e.g., surface 182, may be coated with, or made of, a material having hydrophylic properties which attract physiological fluid 22 having carbon dioxide therein and repel the oxygen loaded carrier fluid 18. Such a design stabilizes and further separates the parallel flow of oxygen loaded carrier fluid 18 and physiological fluid 22 having carbon dioxide therein. In one example, surface 180 is coated with, or made of a fluorinated compound, such as polytetrafluoroethylene and surface 182 is coated with, or made of polyhydroxyethylmethacrylate. Surfaces 180 and 182 may be coated with, or made of, or similar type materials known to those skilled in art.

Preferably, carrier fluid 18 and physiological fluid 22 are immiscible with each other to stabilize and further separate the parallel flow thereof.

Figure 8A:
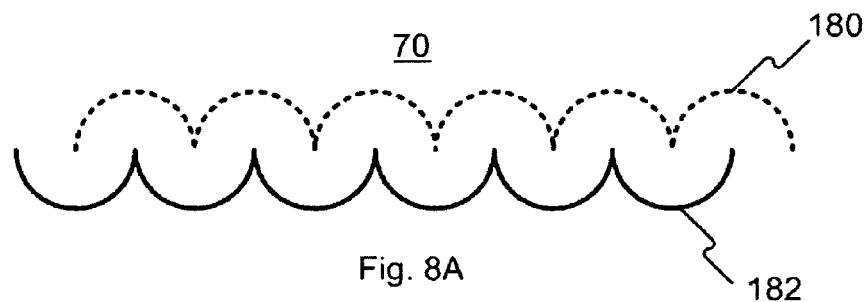
FIG. 8A is a schematic end-view showing one example of the shape of one or more of the microfluidic channels shown in FIG. 6A-7.
Figure 8B:
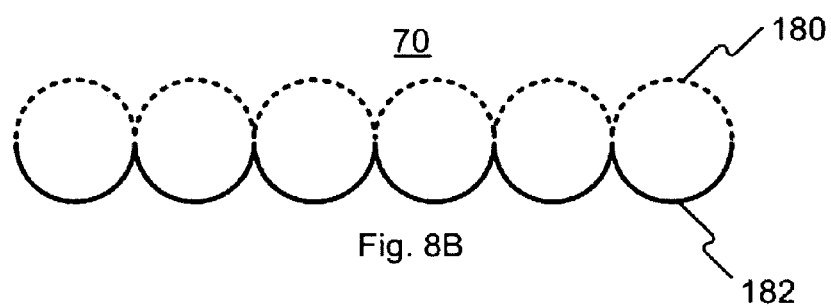
FIG. 8B is a schematic front-view showing another example of the shape of one or more of the microfluidic channels shown in FIG. 6A-7.
Figure 8C:
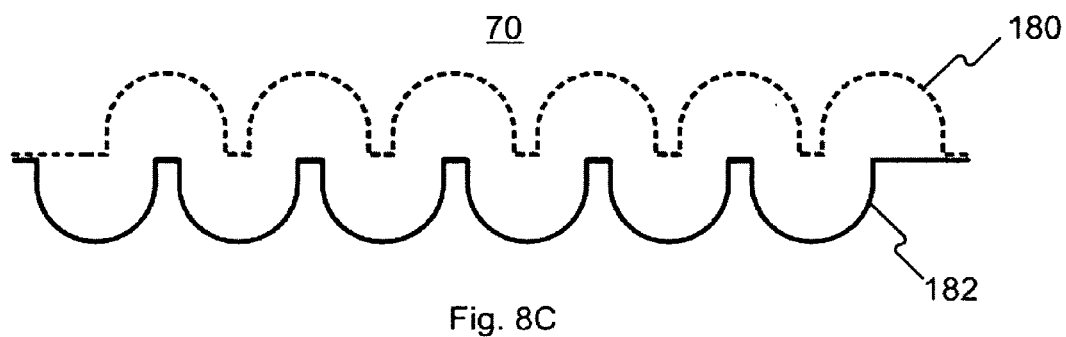
FIG. 8C is a schematic front-view of yet another embodiment of the microfluidic channel shown in FIG. 6A-7.
Figure 8D:
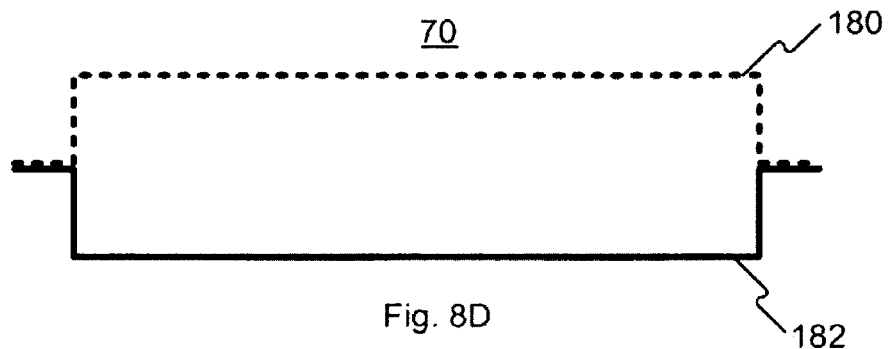
FIG. 8D is a schematic front-view of yet another embodiment of the microfluidic channel shown in FIG. 6A-7.

Microfluidic channel 70, FIGS. 6A-7, with opposing surfaces 180, 182 and/or microfluidic channels 80, 82 (which similarly have opposing surfaces) preferably includes a predetermined shape which increases the surface area thereof in relation to the cross-sectional area of the microfluidic channel to stabilize and further separate the parallel flow of carrier fluid 18 and physiological fluid 22. For example, channel 70 and/or channels 82, 82 may have a scalloped shape as shown in FIG. 8A, a circular shape as shown in FIG. 8B, an offset circular shape as shown in FIG. 8C, or a rectangular shape as shown in FIG. 8D. Other shapes that increase surface area relative to cross-sectional area will be known to those skilled in the art.

Figure 9:
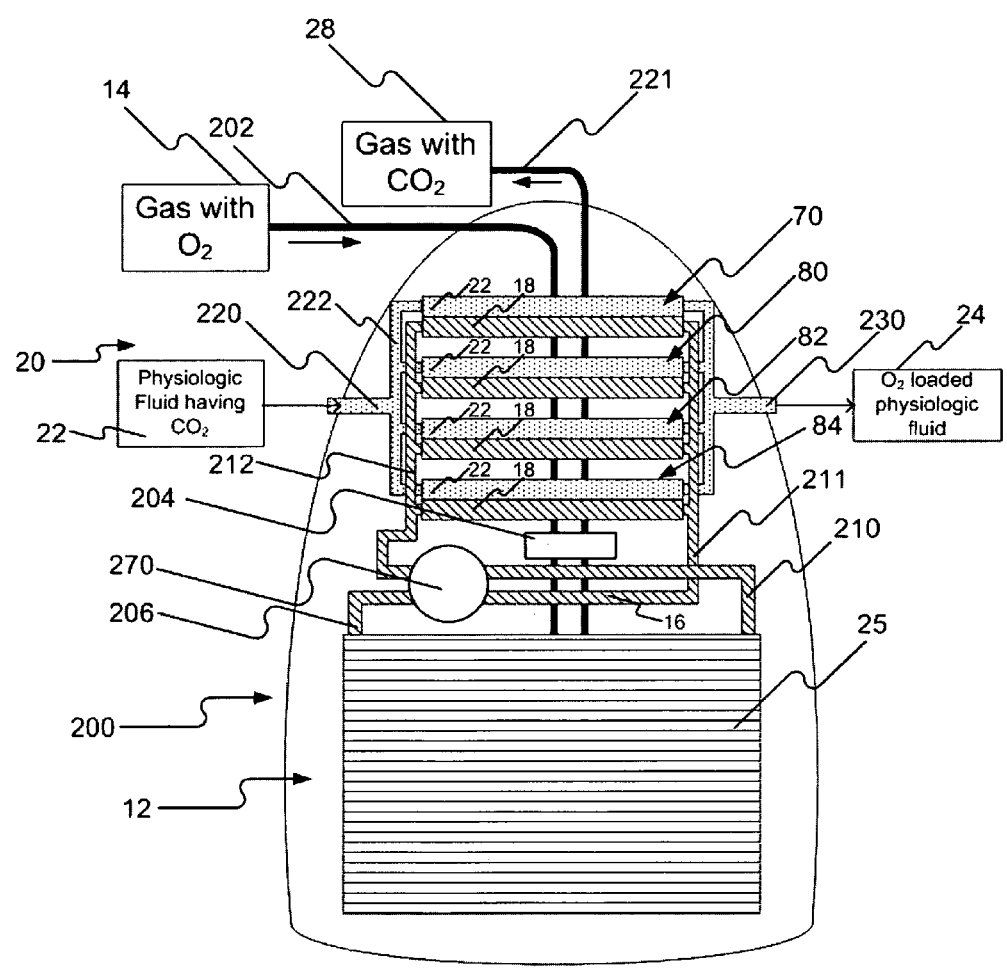
FIG. 9 is a schematic front-view showing one example of the operation of the two-stage system for oxygenating and removing carbon dioxide from a physiological fluid of this invention.
Figure 10:
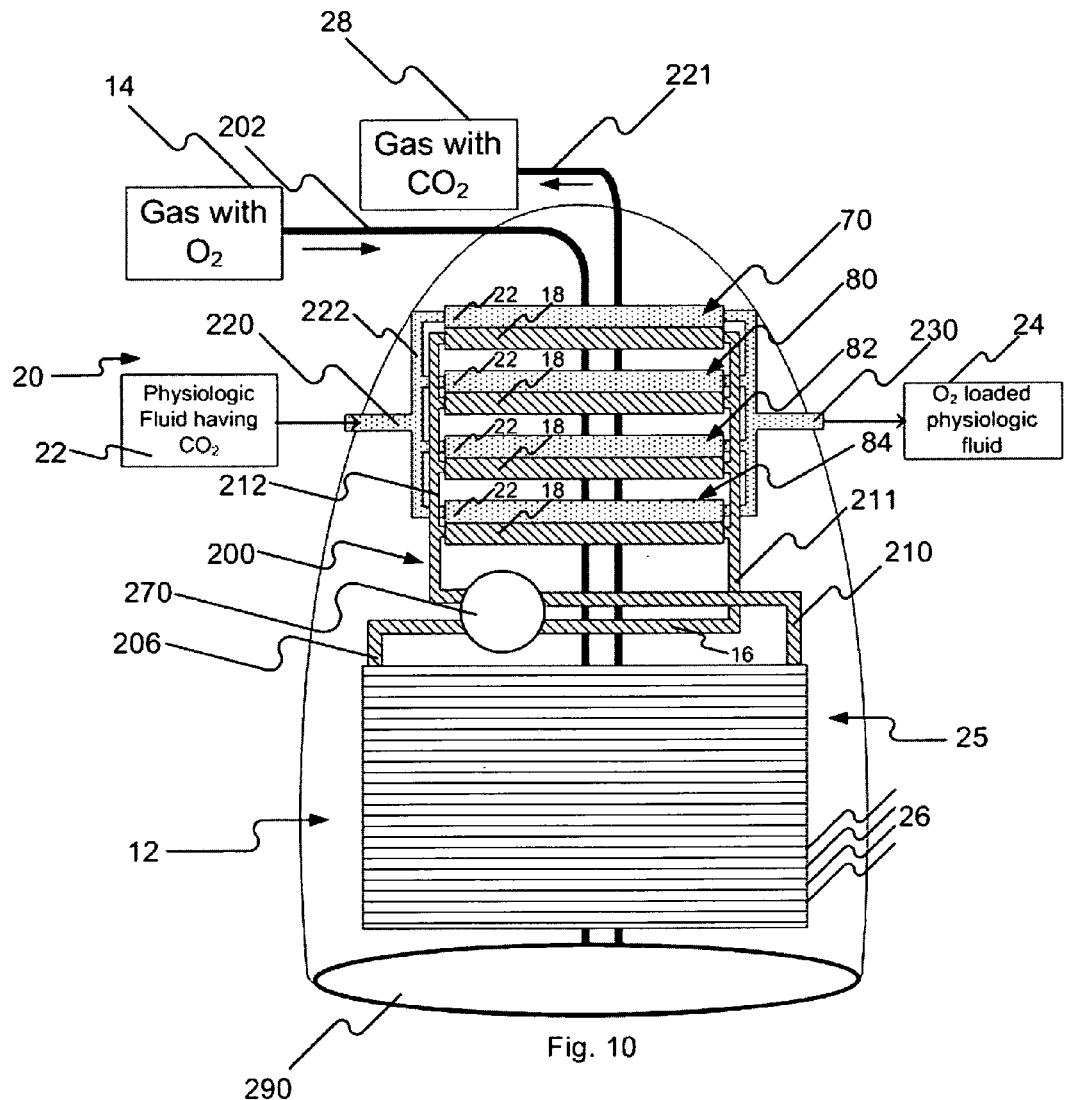
FIG. 10 is a schematic front-view of the system shown in FIG. 9 wherein the blower has been replaced with bellows.

Preferably, microfluidic channel 70 and/or microfluidic channels 80, 82 are made of a bio-compatible material, such as polycarbonate, polyetherimide or similar type materials. In one design, carrier fluid 16 having carbon dioxide therein and/or oxygen loaded carrier fluid 18 may include a perfluro carbon that prevents carrier fluid 16 from mixing with physiological fluid 22 having carbon dioxide therein FIG. 9 shows one embodiment of system 10 which is shaped similar to the shape of a human lung. In this example, primary exchange module 12 includes gas and fluidic distribution subsystem 200 which may include gas inlet and line 202 coupled to array 25 having hollow fibers 26 as discussed above with reference to FIGS. 2-4. In one example, subsystem 200, FIG. 9, may include blower 204, or similar type device, which draws gas 14 have oxygen therein and delivers it to array 25. In another embodiment, bellows 290, FIG. 10, where like parts have been given like numbers, may be used. Subsystem 200, FIG. 9, also includes inlet 206 which is in fluidic communication with secondary exchange module 20. Inlet 206 receives a flow of carrier fluid 16 having carbon dioxide therein from secondary exchange module 22. Gas and fluidic distribution subsystem 200, FIG. 9, also preferably includes fluidic outlet 210 which transfers oxygen loaded carrier fluid 18 via microtubule 212 to microfluidic channels 70, 80, 82, and 84 of secondary exchange module 22, similar as discussed above with reference to FIGS. 6A-7. Gas and fluidic distribution subsystem 200 also includes gas outlet 221 which expels carbon dioxide loaded gas 20 to the environment. Secondary exchange module 20 preferably includes fluidic inlet 220 which receives physiological fluid 22 having carbon dioxide therein. Inlet 220 is in fluidic communication via microtubule 222 to each of channels 70, 80, 82, and 84. Microfluidic channels 70, 80, 82, and 84 create a parallel flow of physiological fluid 22 having carbon dioxide therein and oxygen loaded carrier fluid 18, similar as discussed above with reference to FIGS. 6A-7, to provide the efficient transfer of oxygen from the oxygen loaded carrier fluid 18 to physiological fluid 22 and the transfer of carbon dioxide from physiological fluid 22 to the carrier fluid 18 to create oxygen loaded physiological fluid 24. Secondary exchange module 20 preferably includes outlet 230 in fluidic communication with channels 70, 80, 82, and 84. Outlet 250 is preferably coupled to a vascular system of a patient 120, FIG. 1 to deliver oxygen loaded physiological fluid 24 to vascular system of the patient 120. Secondary exchange module 22 also includes fluidic outlet 211 in fluidic communication with inlet 206 of primary exchange module 12 which transfers carrier fluid 16 having carbon dioxide therein to primary exchange module 12. In one example, pump 270 may be used to drive the transfer of carrier fluid 16 having carbon dioxide therein to primary exchange module 12.

Figure 11:
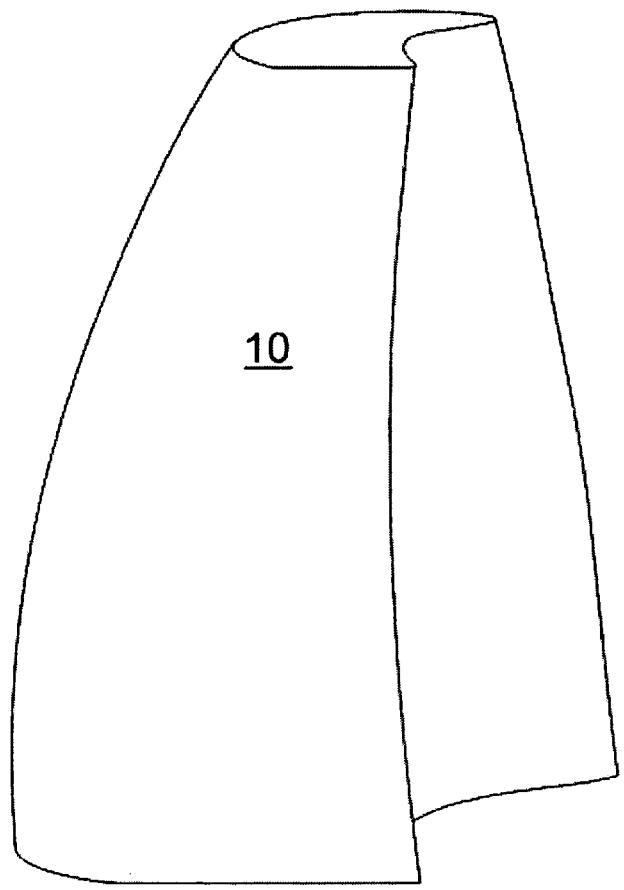
FIG. 11 is a three-dimensional side-view showing one example of the primary exchange module and the secondary exchange module shaped as a lung.
Figure 12:
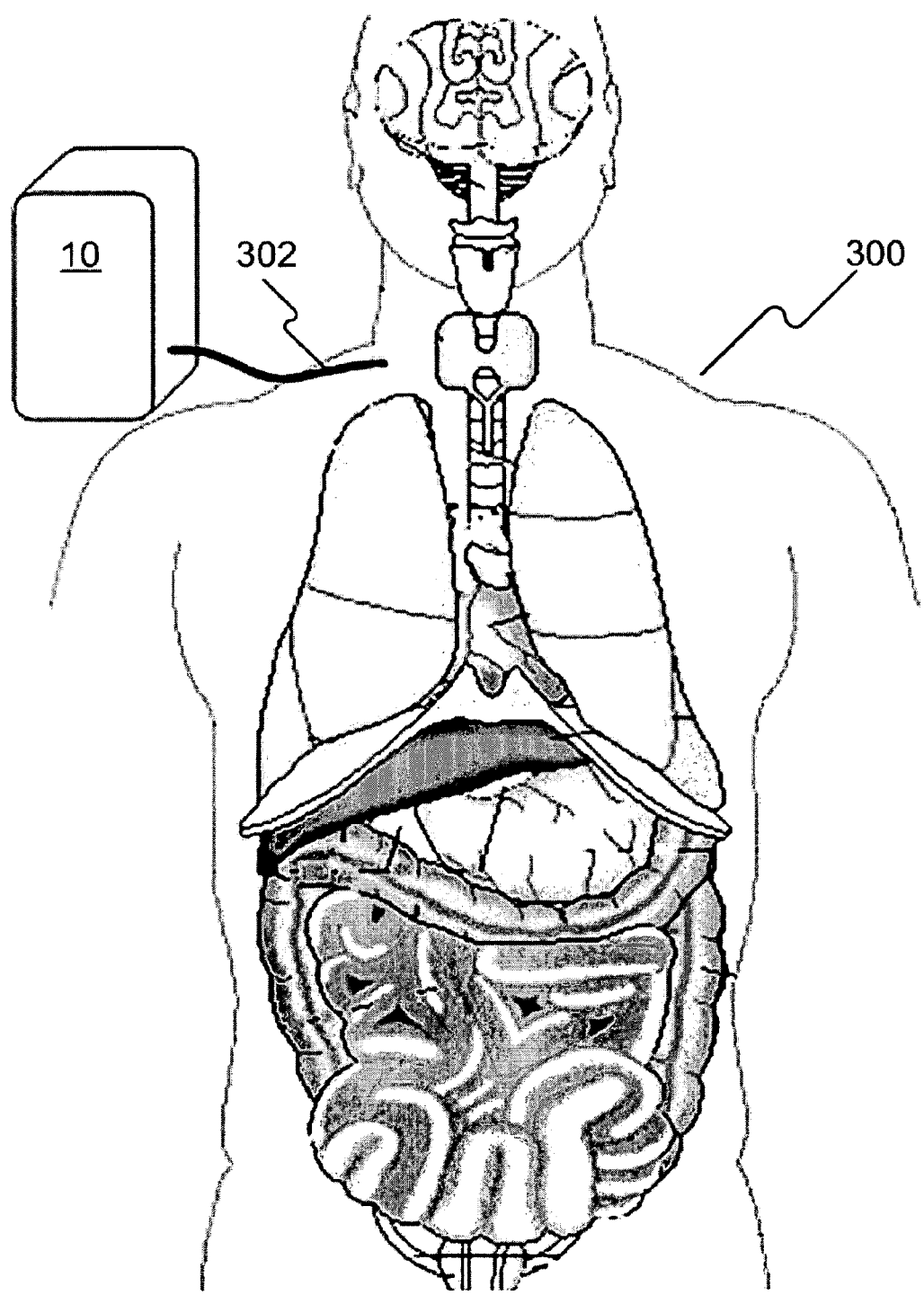
FIG. 12 is a three-dimensional front-view showing one example of the two-stage system of this invention located outside the body of a patient.
Figure 13:
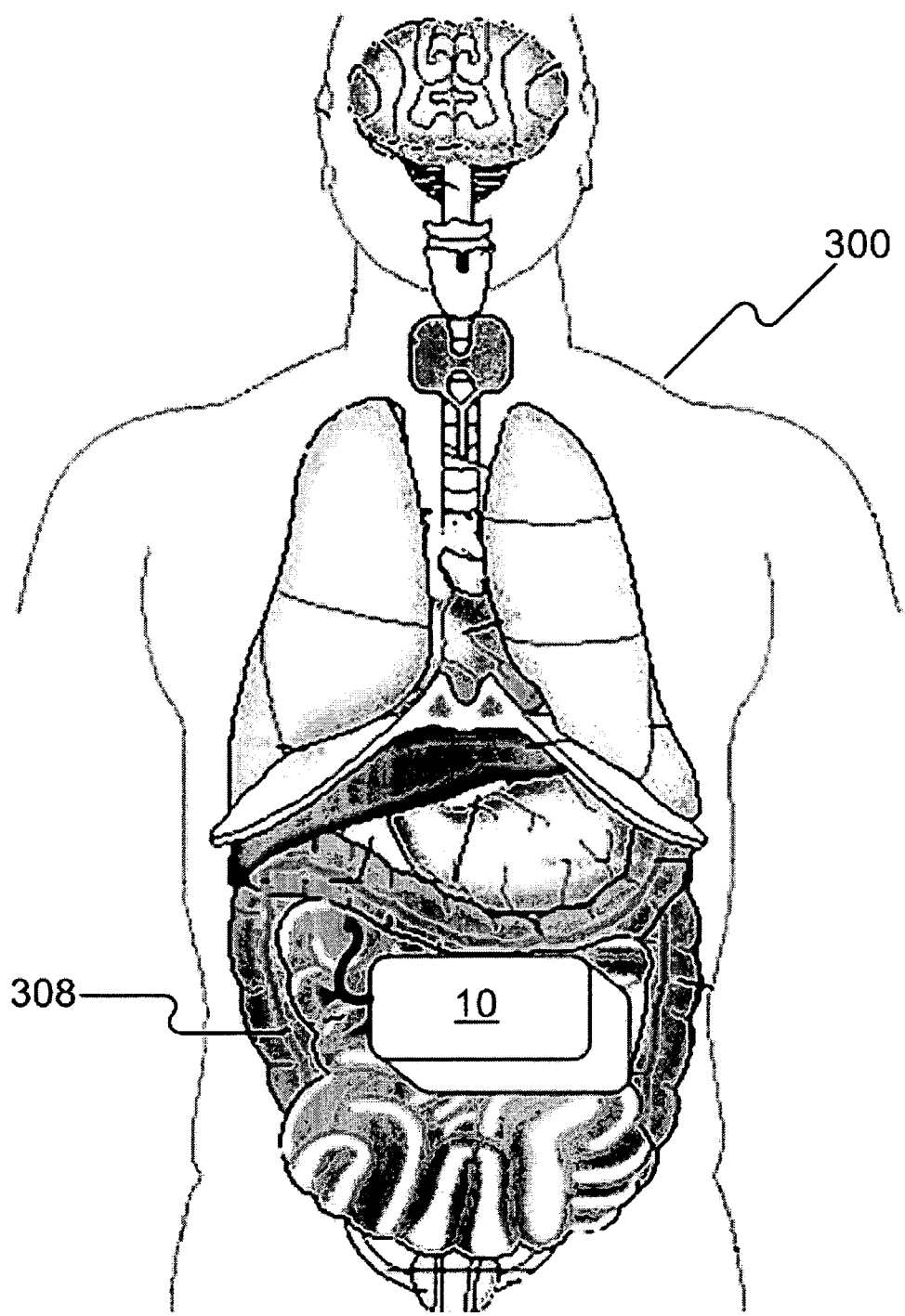
FIG. 13 is a three-dimensional front-view showing one example of the two-stage system of this invention implanted within the abdomen of a patient.
Figure 14:
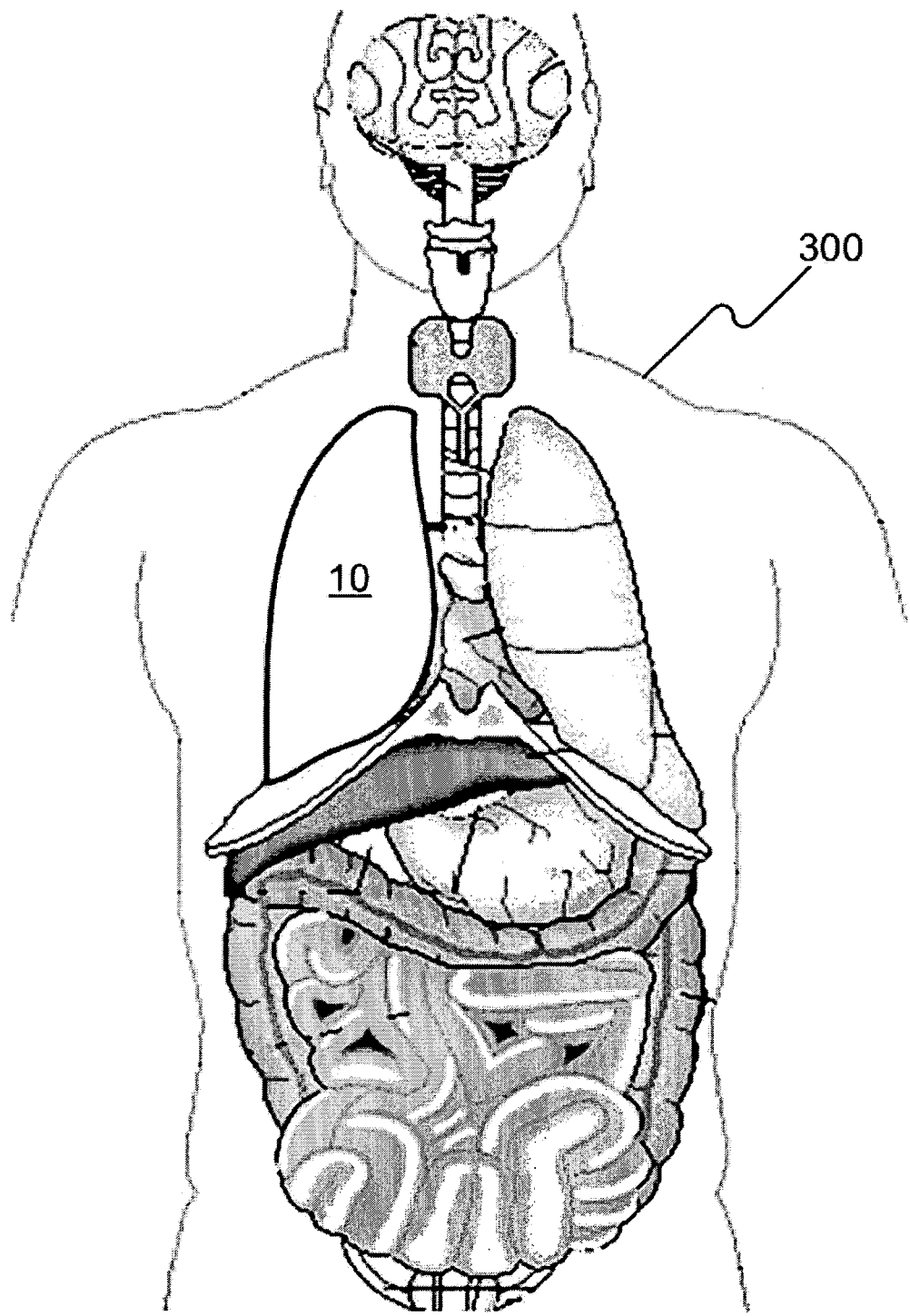
FIG. 14 is a three-dimensional view showing one example of the two-stage system of this invention shaped as a lung and implanted within a patient.

In one embodiment, system 10 with primary exchange module 12 and secondary exchange module 20 may be configured in the shape of a lung as shown in FIG. 11. In another design, system 10 may be located outside the body of patient 300, FIG. 12, and connected to patient 300 by catheter 302. In another example, system 10, FIG. 13, may be implanted within abdomen 308 of patient 300. In yet another example, system 10 may be in the shape of a lung and implanted into patient 300 as shown in FIG. 14.

Mathematical Relationships

The relationship between the length and height of channel 70, FIGS. 6A-10, and/or channels 80, 82, and 84 may be derived from Loschmidt's equation, presented below. This describes the diffusion of a solute from a volume of height d having an initial concentration of solute into an equal height solute-free volume. Initially, the two volumes are separated by a partition. At time t=0, the partition is removed and the extraction fraction E (fraction of solute in first volume that diffuses into second volume) is given by:

$$E = \frac{1}{2} - \frac{4}{\pi^2} \sum_0^\infty \frac{1}{(2n+1)^2} \exp\left[-(2n+1)^2 \left(\frac{\pi}{2d}\right)^2 Dt\right] \quad (1)$$

where D is the diffusivity of the solute in the solvent, in this case, oxygen in the physiological fluid.

Equation (1) can be applied to the diffusion process by considering the flow in the channel to consist of contacting slugs of physiological fluid, e.g., blood, and carrier fluid that move through the channel in unison. The time over which diffusion occurs between the two slugs is the time it takes them to pass through the channel. With these assumptions and after significant algebraic manipulation, Equation (1) can be reformulated into the following:

$$L = \sqrt{\frac{\alpha b \dot{Q}_{b,total}}{nD}} \quad (2)$$

where L is the diffusion channel length in mm, $\alpha$ is the diffusion channel length relative to width W, i.e., its aspect ratio L/W, b is the physiological fluid sheet thickness in mm, $\dot{Q}_{b,total}$ is the total physiological fluid flow into the microfluidic channel, n is the number of diffusion channels connected in parallel, and D is the diffusion coefficient of oxygen in physiological fluid. The diffusion coefficient is used for oxygen since it is the limiting factor over the far higher diffusion coefficient of carbon dioxide. For a total physiological fluid flow of about 6 L/min, a diffusion coefficient of oxygen in blood of $3.0E-04$ mm$^2$/sec and a diffusion channel aspect ratio of 3, Equation (2) reduces to:

$$L = 1E04\sqrt{(b/n)} \quad (3)$$

The diffusion of oxygen in physiological fluid is somewhat complicated by the binding of oxygen to hemoglobin, so the above equations take into account only the noncellular portion, which is the limiting factor. The corresponding pressure drop for a two-layer flow in the diffusion channel can be obtained since the flow in the channel is laminar (a critical requirement to avoid turbulent mixing of the blood and carrier fluids) and by assuming that the flow is fully developed flow, with the standard characteristics of a parabolic flow profile. If the ratio of physiological fluid viscosity to carrier fluid viscosity is denoted by $\chi$, and the ratio of carrier fluid flow height d to blood sheet height b is denoted by z, i.e., $$x = \frac{\mu_b}{\mu_d}; \ z = \frac{d}{b} \quad (4)$$

the resultant pressure drop is:

$$\Delta P = \frac{-12\alpha\mu_b \dot{Q}_{b,total}}{nb^3[1 + 6x \cdot z \cdot (z+1)]} \quad (5)$$

where $\mu_b$ is the physiological fluid viscosity. Using the channel parameters defined relative to Equation 3, a physiological fluid viscosity of 2.0 cp (0.0020 Pa-sec), a carrier fluid viscosity that is 125% of the blood viscosity ($\chi$=0.8), and a physiological fluid sheet height equal to the height of each of the adjoining carrier fluid layer (z=1), Equation 5 reduces to:

$$\Delta P = \frac{0.034}{nb^3} \quad (6)$$

where $\Delta P$ is in mmHg.

As seen from Equations (3) and (6), the length of the diffusion channel is proportional to the square root of the blood sheet height b, while the channel pressure drop is inversely proportional to b$^3$. Given this, b=0.1 mm and n=1000 represent a judicious selection of both parameters. The corresponding diffusion channel length and pressure drop given by Equations (3) and (6) are:

$$L = 1E04\sqrt{(b/n)} = 1E04\sqrt{(0.1/1000)} = 100 \text{ mm} \quad (7)$$

$$\Delta P = 0.034/(1000*0.1^3) = 0.034 \text{ mmHg} \quad (8)$$

The pressure drop is that of the diffusion channel only. This low pressure drop will account for additional pressure drops across the geometries required to bring physiological fluid to the multiple parallel channels while still allowing two-stage gas exchange system 10 to drive physiological fluid through the system using the heart. In addition, this geometry will allow the system to maintain the required cross section of physiological fluid within half of the lung volume. Two-stage system 10 may be designed in variations while staying closely related to the system's design based on the above equations.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A two-stage system for oxygenating and removing carbon dioxide from a physiological fluid, the system comprising:
    a primary exchange module configured to receive a gas having oxygen therein and a carrier fluid having carbon dioxide therein, the primary exchange module configured to transfer oxygen from the gas to the carrier fluid and transfer carbon dioxide from the carrier fluid to the gas to create an oxygen loaded carrier fluid and a carbon dioxide loaded gas; and
    a secondary exchange module configured to receive the oxygen loaded carrier fluid and a physiological fluid having the carbon dioxide therein, the secondary exchange module configured to transfer the oxygen from the oxygen loaded carrier fluid to the physiological fluid and transfer carbon dioxide from the physiological fluid to the carrier fluid to create an oxygen loaded physiological fluid without a membrane between the oxygen loaded carrier fluid and the physiological fluid.

2. The system of claim 1 in which the primary exchange module includes a gas and fluidic distribution subsystem including one or more of:
    a gas inlet configured to receive the gas having the oxygen therein;
    a fluidic inlet in fluidic communication with the secondary exchange module configured to receive the carrier fluid having carbon dioxide therein;

a fluidic outlet in fluidic communication with the secondary exchange module configured to transfer the oxygen loaded carrier fluid to the secondary exchange module; and a gas outlet configured to expel the carbon dioxide loaded gas from the primary exchange module.

3. The system of claim 2 in which the gas having the oxygen therein includes one or more of: ambient air, oxygen gas, and a gas containing oxygen.

4. The system of claim 1 in which the secondary exchange module includes a fluidic distribution subsystem including one or more of:

a first fluidic inlet in fluidic communication with the primary exchange module configured to receive the oxygen loaded carrier fluid;

a second fluidic inlet in fluidic communication with the physiological fluid having the carbon dioxide therein;

a first fluidic outlet in fluidic communication with the primary exchange module configured to transfer the carrier fluid having carbon dioxide therein to the primary exchange module; and a second fluidic outlet configured to transfer the oxygen loaded physiological fluid to the vascular system of the patient.

5. The system of claim 4 in which the second fluidic inlet and/or the second fluidic outlet is coupled to the vascular systems of a patient.

6. The system of claim 1 in which the primary exchange module includes at least one array having plurality of hollow fibers configured to receive the gas having the oxygen therein and in fluidic communication with the carrier fluid having carbon dioxide therein, the at least one array configured to provide the transfer of the oxygen from the gas to the carrier fluid and the transfer of the carbon dioxide from the carrier fluid to the gas.

7. The system of claim 6 in which the distance between one or more and/or each of the plurality of hollow fibers is configured to provide a said transfer of oxygen and said transfer of carbon dioxide.

8. The system of claim 7 in which the plurality of fibers is configured such that the distance between one or more and/or each of the plurality of fibers is smaller than or equal to the outer diameter of one or more and/or each of the plurality of fibers.

9. The system of claim 8 in which the at least one array includes a plurality of headers configured to align the plurality of hollow fibers in a predetermined orientation.

10. The system of claim 1 in which the secondary exchange module includes at least one microfluidic channel in fluidic communication with the oxygen loaded carrier fluid and the physiological fluid having carbon dioxide therein configured to create a parallel flow of the oxygen loaded carrier fluid and the physiological fluid having carbon dioxide therein to provide said transfer of oxygen and said transfer of carbon dioxide.

11. The system of claim 10 in which the at least one microfluidic channel is configured with a predetermined height to create said parallel flow.

12. The system of claim 11 in which the at least one microfluidic channel is configured with a predetermined height to reduce the Reynolds number such that the effective viscosity of the oxygen loaded carrier fluid and the physiological fluid is increased to maintain said parallel flow.

13. The system of claim 12 in which the predetermined height is less than or equal to about 1 mm.

14. The system of claim 10 in which the at least one microfluidic channel includes at least two opposing surfaces.

15. The system of claim 14 in which the opposing surfaces are coated with and/or made of a material configured to stabilize and further separate said parallel flow.

16. The system of claim 15 in which one of the opposing surfaces is coated with and/or made of a material having hydrophilic properties configured to attract the physiological fluid and repel the oxygen loaded carrier fluid to stabilize and further separate said parallel flow.

17. The system of claim 15 in which one of the opposing surfaces is coated with and/or made of a material having hydrophobic properties configured to attract the oxygen loaded carrier fluid and repel the physiological fluid to stabilize and further separate said parallel flow.

18. The system of claim 10 in which the carrier fluid and the physiological fluid are configured to be immiscible with each other to stabilize and further separate said parallel flow.

19. The system of claim 10 in which the at least one microfluidic channel includes a predetermined shape configured to increase the surface area of the microfluidic channel in relation to the cross-sectional area of the microfluidic channel to stabilize and separate said parallel flow.

20. The system of claim 19 in which the predetermined shape includes one or more of: a rectangular shape, a circular shape, an offset circular shape, and a scallop shape.

21. The system of claim 10 in which the at least one microfluidic channel is made of bio-compatible material.

22. The system of claim 10 in which the at least one microfluidic channel is housed in a chamber.

23. The system of claim 10 in which the at least one microfluidic channel includes a plurality of microfluidic channels.

24. The system of claim 1 in which the carrier fluid includes perfluorocarbon.

25. The system of claim 1 in which the primary exchange module includes a blower and/or plurality of bellows configured to deliver the gas having oxygen therein thereto.

26. The system of claim 1 in which the primary exchange module and the secondary exchange module are located external from the patient.

27. The system of claim 1 in which the primary exchange module and the secondary exchange module are implanted within a patient.

28. The system of claim 1 in which the primary exchange module and the secondary exchange module are configured in the shape of a lung.

29. The system of claim 28 in which the system is implanted within the thoracic cavity of a patient.

* * * * *

UNITED STATES PATENT AND TRADEMARK OFFICE
CERTIFICATE OF CORRECTION

PATENT NO. : 8,574,309 B2  
APPLICATION NO. : 12/931764  
DATED : November 5, 2013  
INVENTOR(S) : Galea et al.

Page 1 of 1

It is certified that error appears in the above-identified patent and that said Letters Patent is hereby corrected as shown below:

In the specification

Col. 1 at lines 7-11 "This invention was made with U.S. Government support under Grant Nos. 6R43HL074456-02 and 1R43HL091593-01, both awarded by the National Institutes of Health. The United States Government may have certain rights in certain aspects of the invention." should read --"This invention was made with government support under Grant Nos. 6R43HL074456-02 and 1R43HL091593-01, both awarded by the National Institutes of Health. The government has certain rights in the invention."--.

Signed and Sealed this  
Seventeenth Day of May, 2016

Michelle K. Lee  
*Director of the United States Patent and Trademark Office*